(12) United States Patent
Albiol et al.

(10) Patent No.: US 9,406,496 B2
(45) Date of Patent: Aug. 2, 2016

(54) METHOD AND SYSTEM FOR IMPROVING CHARACTERISTIC PEAK SIGNALS IN ANALYTICAL ELECTRON MICROSCOPY

(71) Applicants: Universitat de Barcelona, Barcelona (ES); Nanomegas SPRL, Molenbeek-Saint-Jean (BE); AppFive LLC, Tempe, AZ (US)

(72) Inventors: Sonia Estrade Albiol, Barcelona (ES); Joaquin Portillo Serra, Barcelona (ES); Francisca Peiró Martinez, Barcelona (ES); José Manuel Rebled Corsellas, Tarragona (ES); Lluís Yedra Cardona, Barcelona (ES); Stavros Nicolopoulos, Valencia (ES); Steven Kim, Phoenix, AZ (US); Jon Karl Weiss, Tempe, AZ (US)

(73) Assignees: UNIVERSITAT DE BARCELONA, Barcelona (ES); NANOMEGAS SPRL, Molenbeek-Saint-Jean (ES); APPFIVE LLC, Tempe, AZ (US)

( * ) Notice: Subject to any disclaimer, the term of this patent is extended or adjusted under 35 U.S.C. 154(b) by 0 days.

(21) Appl. No.: 13/681,245

(22) Filed: Nov. 19, 2012

(65) Prior Publication Data

US 2013/0240728 A1     Sep. 19, 2013

(30) Foreign Application Priority Data

Mar. 19, 2012   (EP) ..................... 12160112

(51) Int. Cl.
*G01N 23/225*  (2006.01)
*H01J 49/44*  (2006.01)
*H01J 37/28*  (2006.01)

(52) U.S. Cl.
CPC ............ *H01J 49/44* (2013.01); *G01N 23/2251* (2013.01); *G01N 2223/051* (2013.01);

(Continued)

(58) Field of Classification Search
CPC ............ G01N 23/2252; G01N 23/2251; H01J 2237/1505; H01J 2237/1506; H01J 2237/1507
USPC ............................................. 250/311
See application file for complete search history.

(56) References Cited

U.S. PATENT DOCUMENTS 4,742,223 A * 5/1988 Kesmodel ............... H01J 49/48
250/305
5,350,921 A * 9/1994 Aoyama et al. ............... 250/311

(Continued)

FOREIGN PATENT DOCUMENTS

EP    1665321 B1   11/2009
WO   2005022852    3/2005

(Continued)

OTHER PUBLICATIONS

Okayama, "Electron-beam Lithography System Using a Quadrupole Triplet", JVST B, 6, (1) (1988).*

(Continued)

*Primary Examiner* — Jack Berman
*Assistant Examiner* — James Choi
(74) *Attorney, Agent, or Firm* — Avery N. Goldstein; Blue Filament Law PLLC

(57) ABSTRACT

A method and system are disclosed for improving characteristic peak signals in electron energy loss spectroscopy (EELS) and energy dispersive x-ray spectroscopy (EDS) measurements of crystalline materials. A beam scanning protocol is applied which varies the inclination, azimuthal angle, or a combination thereof of the incident beam while spectroscopic data is acquired. The method and system may be applied to compositional mapping.

23 Claims, 6 Drawing Sheets

(52) U.S. Cl.
CPC ........... *G01N2223/402* (2013.01); *H01J 37/28* (2013.01); *H01J 2237/1505* (2013.01); *H01J 2237/1506* (2013.01); *H01J 2237/1507* (2013.01); *H01J 2237/2808* (2013.01)

(56) References Cited

U.S. PATENT DOCUMENTS

| | | | | |
|---|---|---|---|---|
| 5,576,543 | A * | 11/1996 | Dingley | 250/311 |
| 7,202,475 | B1 * | 4/2007 | Testoni | 250/310 |
| 8,076,640 | B2 | 12/2011 | Koch | |
| 2002/0096632 | A1 * | 7/2002 | Kaji | G01N 23/2251 250/305 |
| 2003/0025075 | A1 * | 2/2003 | Zaluzec | 250/306 |
| 2004/0183012 | A1 * | 9/2004 | Yaguchi et al. | 250/306 |
| 2006/0034543 | A1 * | 2/2006 | Bacus et al. | 382/284 |
| 2006/0043291 | A1 * | 3/2006 | Peng | H01J 37/28 250/310 |
| 2007/0023659 | A1 * | 2/2007 | Sergeevich et al. | 250/311 |
| 2008/0275655 | A1 * | 11/2008 | Moeck | G01N 23/04 702/27 |
| 2011/0107472 | A1 * | 5/2011 | Han et al. | 850/53 |
| 2011/0108736 | A1 * | 5/2011 | Preikszas | H01J 37/1478 250/397 |
| 2012/0001069 | A1 * | 1/2012 | Kashihara | 250/310 |
| 2015/0076346 | A1 * | 3/2015 | Weiss | H01J 37/26 250/307 |

FOREIGN PATENT DOCUMENTS

| | | |
|---|---|---|
| WO | 2008060237 | 5/2008 |
| WO | 2010052289 | 5/2010 |

OTHER PUBLICATIONS

A.S. Eggeman, T.A. White, P.A. Midgley, Is Precession Electron Diffraction Kinematical? Part II: A Practical Method to Determine the Optimum Precession Angle, Ultramicroscopy, 110 (21010), pp. 771-777.
Frederick Meisenkothen, Robert Wheeler, Michael D. Uchic, Robert D. Kerns, Frank J. Scheltens, Electron Channeling: A Problem for X-Ray Microanalysis in Materials Science, Microscopy and Microanalysis, 15 (2009), pp. 83-92.
E. Mugnaioli, T. Gorelik, U. Kolb, "Ab initio" Structure Solution from Electron Diffraction Data Obtaind by a Combination of Automated Diffraction Tomography and Precession Technique, Ultramicroscopy, 109 (2009), pp. 758-765.
J.M. Rebled, Li. Yedra, S. Estrade, J. Portillo, F. Peiro, A New Approach for 3D Reconstruction from Bright Field TEM Imaging: Beam Precession Assisted Electron Tomography, Ultramicroscopy, (2011).
S. Van Aert, P. Geuens, D. Van Dyck, C. Kisielowski, J.R. Jinschek, Electron Channelling Based Crystallography, Ultramicroscopy, 107, (2007), 551-558.
R. Vincent, P.A. Midgley, Double Conical Beam-Rocking System for Measurment of Integrated Electron Diffraction Intensities, Ultramicroscopy, 53, (1994), 271-282.
T.A. White, A.S. Eggeman, P.A. Midgley, Is Precession Electron Diffraction Kinematical? Part I: "Phase-Scrambling" Multislice Simulations, Ultramicroscopy, 110, (2010), 763-770.
L.J. Allen, S.D. Findlay, A.R. Lupini, M.P. Oxley, S.J. Pennycook, Atomic-Resolution Electron Energy Loss Spectroscopy Imaging in Aberration Corrected Scanning Transmission Electron Microscopy, Physical Review Letters, 91(10), 2003.
H.E. Bishop, The Influence of Diffraction Effects on Quantitative Auger Electron Spectroscopy, Surface and Interface Analysis, 16, (1990); pp. 118-128.
Joke Hadermann, Artem M. Abakumov, Tyche Perkisas, Hans D'Hondt, Haiyan Tan, Johan Verbeeck, Vladimir P. Filonenko, Evgeny V. Antipov, Gustaaf Van Tendeloo, New Perovskite-Based Manganite, Journal of Solid State Chemistry, 183, (2010), 2190-2195.
Joaquim Portillo, Edgar F. Rauch, Stavros Nicolopoulos, Mauro Gemmi, Daniel Bultreys, Precession Electron Diffraction Assisted Orientation Mapping in the Transmission Electron Microscope, Materials Science Forum, 664 (2010), pp. 1-7.
Zhang, Daliang et al., Collecting 3D Electron Diffraction Data by the Rotation Method, Z. Kristallogr. 225 (2010), pp. 94-102, München.
Gatan Image Filter User Manual, Apr. 1996.
J. Ciston, B. Deng, L.D. Marks, C.S. Own, W. Sinkler; "A quantitative analysis of the cone-angle dependence in precession electron diffraction", Ultramicroscopy 108 (2008) 514-522.
Wu, J.S. et al. "Structural Study of New Hydrocarbon Nano-Crystals by Energy-Filtered Electron Diffraction", Science d Direct; www.sciencedirect.com; www.elsevier.com/locate/ultramic; 2004, pp. 1-6.
Avilov, A.S. "Quantitative Electron Diffraction Structure Analysis (EDSA)" Theory and Practise of Determining the Electrostatic Potential and Chemical Bonding in Crystals; T.E. Weirich et al. (eds.), Electron Crystallography, pp. 97-120. © 2006 Springer. Printed in the Netherlands.
Avilov, A.S., et al. "Scanning System for High-Energy Electron Diffractometry" Reasearch Papers Journal of Applied Crystallography (1999). pp. 32, 1033-1038. © 1999 International Union of Crystallography, Printed in Great Britain.
Avilov, A.S., et al. "Precision Electron Diffraction Structure Analysis and Its Use in Physics and Chemistry of Solids", Crystallography Reports, vol. 46, No. 4, 2001, pp. 556-571. Translated from Kristollografiya, vol. 46, No. 4, 2001, pp. 620-635. Original Russian Text Copyright © 2001 by Avilov, Tsirelson. pp. 556 to 571. Feb. 22, 2001.
S. Estrade et al., EELS Signal Enhancement by Means of Beam Precession in the TEM. Ultramicroscopy, vol. 116, at pp. 135-137 (May 2012).
Y. Liao and L.D. Marks, Reduction of Electron Channeling in EDS using Precession, Ultramicroscopy, vol. 126, at pp. 19-22 (Mar. 2013).

* cited by examiner

METHOD AND SYSTEM FOR IMPROVING CHARACTERISTIC PEAK SIGNALS IN ANALYTICAL ELECTRON MICROSCOPY

RELATED APPLICATIONS

This application claims priority benefit of EP Application 12160112.4 filed 19 Mar. 2012; the contents of which are hereby incorporated by reference.

FIELD OF THE INVENTION

The invention relates to the use in electron microscopy of electron energy loss and energy dispersive x-ray spectroscopy for determining the local chemical composition of materials. More specifically, it relates to quantitative measurements of characteristic peak signals obtained from samples containing crystalline regions and the generation of compositional maps from such samples.

BACKGROUND

Analytical electron microscopy is frequently used to investigate the chemical composition of materials down to sub-nanometer length scales. Electron energy loss spectroscopy ("EELS") relies on measurements of the energy distribution of incident electrons transmitted through the microscope sample, while energy dispersive x-ray spectroscopy ("EDS") relies on measurements of the energy distribution of x-rays emitted from regions of the sample exposed to the incident electron beam. Though these two techniques originate in inelastic scattering phenomena, the processes by which the incident high energy electron beam excites bound state electrons within the sample, they differ in their ease of applicability to different elements. Generally, EELS is better suited to lighter elements—corresponding to characteristic energy losses up to about 3 keV—while EDS is better suited to heavier elements—corresponding to characteristic x-ray energies up to about 30 keV. Because EELS relies on transmitted electrons, it is used almost exclusively in transmission electron microscopy ("TEM") and scanning transmission electron microscopy ("STEM"). Because EDS does not rely on transmitted electrons, it can be used in TEM and STEM, and also in scanning electron microscopy ("SEM"), which does not require electron transparent samples.

In EELS and EDS, quantitative chemical information is obtained by measuring the intensity of the characteristic peaks (also called "edges" in EELS, in recognition of their distinctive shape) associated with particular elements, which are often observed against a highly non-uniform background. The strength of signal associated with a given peak or peaks, and thus the accuracy and sensitivity of the measurement of the concentration of a given element, can be affected by a range of factors, including local sample composition and morphology, the spatial/energy profile and coherence of the incident beam, and the resolution and other characteristics of the X-ray or EELS detection system, that, taken together, can be extremely difficult to quantify.

When investigating samples comprising regions of crystalline material, the incident beam is frequently aligned close to a high symmetry crystallographic direction (also referred to as a "zone axis"). This can be deliberate—for example, when obtaining atomic resolution images in TEM/STEM or seeking information about crystallographic defects, such as grain boundaries or interfaces—or can occur accidentally, particularly when investigating polycrystalline materials comprised of crystallites having a range of different orientations. In any event, when the incident beam is aligned close to a zone axis, the coherent scattering by the periodic potential of the crystal (so-called elastic scattering) can strongly affect the peak intensities measured in EELS or EDS. In some circumstances, these "channeling" effects can be exploited to provide information about the location, on an atomic scale, of chemical species within a crystal structure. See, e.g., S. Van Aert et al., *Electron Channeling Based Crystallography*, 107 Ultramicroscopy 551-58 (2007). In general, however, channeling makes it more difficult to extract meaningful compositional information from crystalline samples. For example, a change of only one degree in the orientation of the incident electron beam can lead to changes of as much as 20% in the apparent relative composition of two elements, as measured by the strength of the characteristic x-ray signal. See, e.g., Frederick Meisenkothen et al., *Electron Channeling: A Problem for X-Ray Microanalysis in Materials Science*, 15 Microscopy and Microanalysis 83-92 (2009). Having a beam orientation close to a zone axis can also reduce the overall intensity of EELS and EDS peaks relative to the background, increasing the stochastic noise and the uncertainty of quantitative measurements.

Elemental composition maps can be generated by performing quantitative EELS or EDS peak measurements at multiple sample locations, assuming the difficulties noted above, associated with spectrum acquisition from discrete locations, can be overcome. When generating compositional maps, further difficulties are associated with the need to move the beam between different locations while maintaining consistent data collection conditions over extended time periods. These difficulties include sample degradation and drift and changes in signal intensity arising from electron optical, mechanical and electronic instabilities. Further, the changes in EELS or EDS peak intensities from crystalline samples associated with small changes in the angle of the incident beam are of particular concern for compositional mapping, since the relative angle of the incident beam can be affected as the beam is moved between locations by changes in electron optical conditions or sample morphology. Such changes in relative incident beam angle with location are almost inevitable in studies of polycrystalline materials, which, as noted above, generally contain a range of differently orientated crystallites.

Unlike the peaks used for quantitative compositional analysis in EELS and EDS, which originate from the interaction of the high energy electron beam with electrons bound to individual atoms, quantitative structural analysis by electron diffraction relies on measurements of the intensities of diffracted beams that originate from the interaction of high energy electron beam with the periodic potential of the crystal. Like the peaks in EDS and EELS, the intensity of these diffracted beams can be strongly affected by a range of factors that are not always easily quantifiable, including local sample composition and morphology, and variations in the spatial/energy profile and coherence of the incident beam. Further, when the incident beam is aligned along a high symmetry crystallographic orientation, as is generally required for meaningful structural analysis, intensity is dynamically redistributed between the incident and multiple diffracted beams in a complicated and not readily quantifiable manner.

Structural analysis of crystalline materials using transmission electron diffraction can be facilitated by applying a modification of the Buerger x-ray diffraction technique known as precession electron diffraction ("PED"), in which the incident electron beam (normally aligned with the optical axis of the electron microscope) is inclined away from and rotated ("precessed") around a high symmetry crystallographic direction of the fixed TEM sample, and in which transmitted beams are de-scanned using a complimentary precession algorithm to re-align them with the optical axis of the electron microscope. See R. Vincent & P. A. Midgley, *Double Conical Beam-rocking System for Measurement of Integrated Electron Diffraction Intensities*, 53 Ultramicroscopy 271-82 (1994). PED can be qualitatively understood as suppressing the "dynamical" redistribution of intensity between incident and multiple diffracted beams associated with high symmetry directions, thereby approaching the more easily modeled "quasi-kinematical" conditions. However, a full theoretical understanding of the factors that govern the transition from dynamical to quasi-kinematical conditions in PED remains elusive. See E. Mugnaioli et al., "Ab Initio" *Structure Solution from Electron Diffraction Data Obtained by a Combination of Automated Electron Tomography and Precession Technique*, 109 Ultramicroscopy 758-65 (2009); T. A. White et al., *Is Precession Electron Diffraction Kinematical?* [Parts I and II], 110 Ultramicroscopy 763-770 (2010).

For typical TEM accelerating voltages, a relatively large precession angle, typically from 1-3 degrees, is required to suppress dynamical scattering enough to implement PED. The technique has been further developed as a means to facilitate the analysis of complicated phases, including by a combination of PED with x-ray and neutron diffraction data. See EP 1 665 321 B1. A beam scanning protocol analogous to PED—also aimed at achieving quasi-kinematical conditions to facilitate structural analysis—has also been developed, but using an oscillatory or pendulum-like motion ("EDPM") in place of precession. See WO/2008/060237. Other work has applied a beam scanning protocol and transmission electron diffraction to facilitate the acquisition of orientation and structural phase maps (see WO 2010/052289), and to suppress spurious diffraction contrast in TEM images of the same crystallographic feature obtained along different directions. See J. M. Rebled et al., *A New Approach to 3D Reconstruction from Bright Field Tem Imaging: Beam Precession Assisted Electron Tomography*, 111 Ultramicroscopy 1504-11 (2011).

The present invention alleviates many of the difficulties of quantitative EDS and EELS measurements of samples containing crystalline or polycrystalline regions by applying a beam scanning protocol to maximize signal strength and diminish spurious signal variations associated with changes in relative incident beam angle, thereby allowing improved compositional mapping of samples containing crystalline or polycrystalline regions by STEM, TEM and SEM.

SUMMARY OF THE INVENTION

In one embodiment, a method for obtaining spectroscopic data from a sample of crystalline material in an electron microscope is disclosed. The method comprising configuring an electron beam to impinge on a location of the sample comprising a region of crystalline material, applying an incident beam scanning protocol that maintains the beam impinging on substantially the same sample location while varying over time one or both of the incident beam inclination angle and azimuthal angle, and acquiring a set of spectroscopic data while the beam scanning protocol is being applied.

In another embodiment, the spectroscopic data set comprises energy-resolved x-ray data acquired from x-rays emitted from the crystalline region.

In another embodiment, the spectroscopic data set comprises energy loss data acquired from a beam exiting the sample in a transmission electron microscope, with a complementary beam scanning protocol being applied to the exit beam to substantially remove the time-dependent movements arising from the incident beam scanning protocol.

In yet another embodiment, quantitative compositional information is derived from the spectroscopic data set.

In other embodiment, the incident beam scanning protocol is associated with an inclination angle, and the incident beam scanning protocol comprises processing the incident beam at a substantially constant inclination angle.

In yet another embodiment, the incident electron beam without the beam scanning protocol applied is substantially parallel with a high symmetry crystallographic direction of the crystalline region.

In yet a further embodiment, the method further includes identifying a characteristic feature within the spectroscopic data set, acquiring from the location a plurality of data sets comprising the characteristic feature by applying the beam scanning protocol at a range of inclination angles, quantifying the characteristic feature for each of the plurality of data sets; and identifying an optimum inclination angle associated with the characteristic feature. In yet other embodiments, the optimum inclination angle is the minimum inclination angle for which the quantified characteristic feature obtains a maximum value.

Embodiments are disclosed in which the electron microscope comprises a number of beam deflection control circuits and the beam scanning protocol is applied by delivering a number of beam scanning protocol signals to the number of beam deflection control circuits, with the beam scanning protocol signals further comprising one or more of a time-dependent induction compensation component, a distortion compensation component, a lens precession and a lens aberration component.

Also disclosed is a method for generating a composition map comprising applying any of the above methods to a multiplicity of sample locations and mapping the quantitative compositional information from the multiplicity of sample locations and the relative location of the multiplicity of sample locations onto a compositional map.

In another embodiment, a system is disclosed comprising an external beam control device configured to deliver beam scanning protocol signals to the beam deflection control circuits of the electron microscope, with the external beam control device comprising digital to analog converters ("DACs"), each DAC configured to deliver the beam scanning protocol signals to one of the beam deflection control circuits. In other embodiments, a control computer is configured to drive the external beam control device and to acquire and process electron energy loss and x-ray data. In yet another embodiment, the external beam control device is configured to receive and compare images received at different times from a microscope detector and apply drift compensation.

Figure 1:
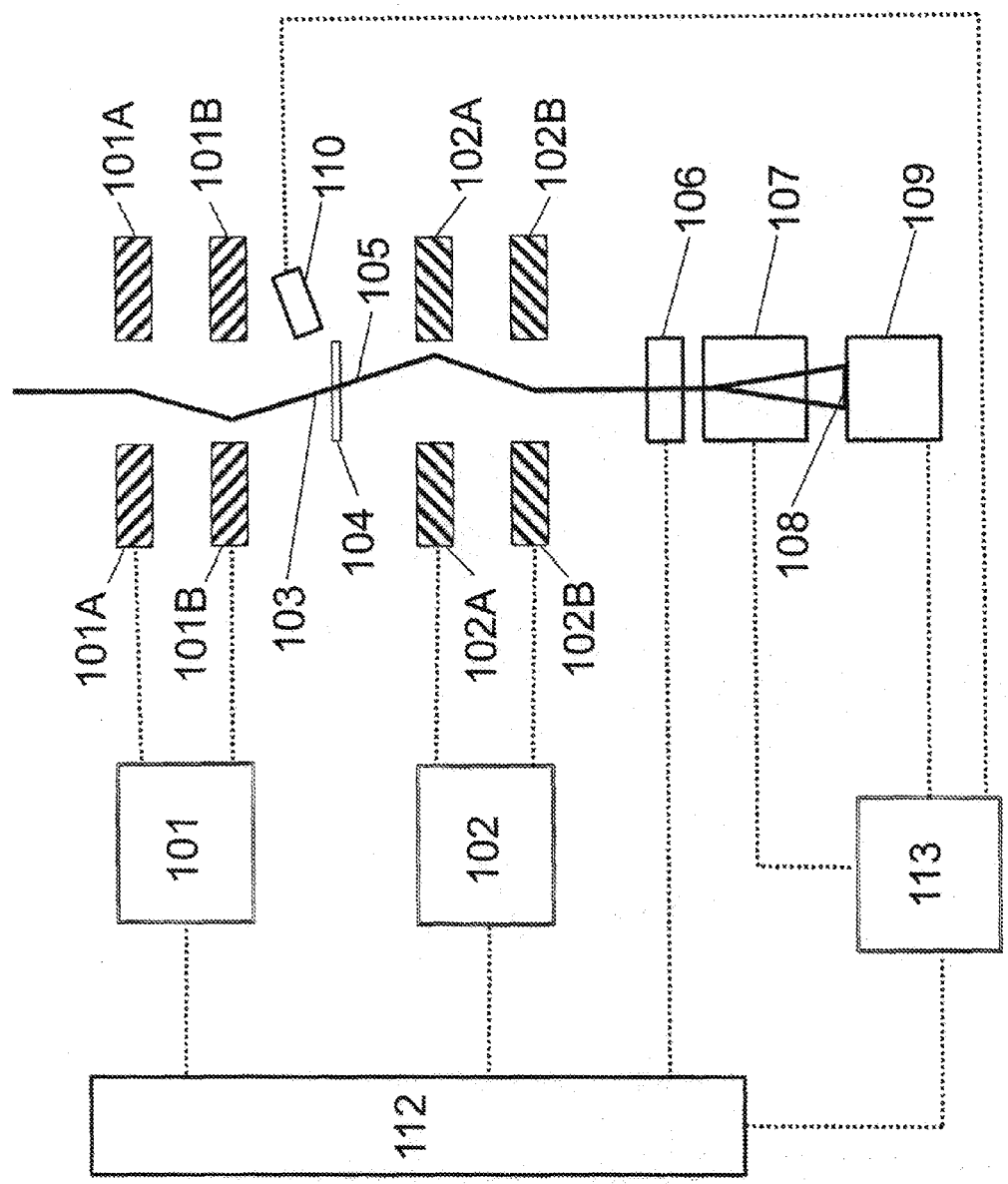
FIG. 1 is a schematic of a TEM configured to practice an embodiment of the invention.

Various features of the invention are described herein with reference to the figures, the written description and claims. These features may be combined with or interchanged in any permutation other than one in which the features are mutually exclusive. Comprising is used to mean including but not limited to the listed features.

DETAILED DESCRIPTION OF THE INVENTION

According to an embodiment of the invention, a beam deflection control device, is directed by a control computer and may be used to apply a beam scanning protocol during acquisition of EDS and/or EELS data to increase signal strength and reduce spurious signal variations. The control computer in other embodiment of the present invention are part of the original system installed in the microscope, or other embodiments is an external unit coupled to an external beam deflection control device. The control computer in certain embodiments of the present invention are configured to acquire and process images from SEM or STEM detectors (brightfield, darkfield, annular darkfield, backscatter, secondary electron, etc.), and acquire and process EDS and EELS data.

As described in more detail below, according to an embodiment of the invention, a given beam scanning protocol may be optimized for characteristic EDS or EELS features corresponding to a given chemical element, allowing quantitative EDS or EELS data for one or more elements to be acquired in multiple locations of a sample for the generation of quantitative compositional maps.

Different scanning protocols may be used in different embodiments of the invention. Precession of the type described by Vincent and Midgley may be used, in which the incident beam remains fixed on substantially the same location in the sample, is deflected by a fixed incident angle away from the unscanned direction (typically aligned with the optic axis of the electron microscope) and rotated rapidly around the azimuth at a uniform rotational speed. Other scanning protocols may involve the incident beam, again remaining fixed on substantially the same location of the sample, executing a series of pendulum-like movements that intersect, or pass close to, the unscanned incident beam direction (typically aligned on or close to the optic axis) and implementing a gradual rotation around the azimuth. In other embodiments, rather than employing a fixed rate of rotation, the incident beam may be rotated at a variable rate or the azimuth may be changed by discrete amounts. Other scanning protocols may be employed, such as, for example, protocols involving directing the beam to conform to a series of discrete incident and azimuth coordinates, or to execute a series of scans between pairs of discrete incident and azimuth coordinates, again without deviating substantially from the location on the sample. As discussed below, the scanning protocol may have a time period with a frequency (or frequencies) adjusted to accommodate the acquisition time required for a particular characteristic peak or peaks. The chosen scanning protocol should have the net effect of imparting sufficient inclination to the incident beam to suppress dynamical scattering sufficiently to improve the strength of a characteristic EDS or EELS feature of interest while also not introducing systematic errors due to over sampling a particular azimuthal angle or set of angles. Further, to the extent a given scanning protocol is to be optimized for analysis a given EDS or EELS feature, an incident angle associated with the scanning protocol should be amenable to identification and control. For example, in a typical precession configuration, the required tilt angle may be set in the range of anywhere from about 0.1 to 2 degrees, possibly as high as 3 degrees, corresponding to the incident angle of the beam scanning protocol, applied with an azimuthal rotation in the range of 10-1000 Hz. Though, for convenience, the examples that follow generally refer to precession angle and a precession frequency, it should be understood that a variety of beam scanning protocols may be implemented in place of precession.

One embodiment, shown in the schematic of FIG. 1, comprises a TEM, typically operating at an accelerating voltage in the range between 20 kV and 300 kV, coupled to an external beam deflection control device 112. The TEM may further include an electron beam monochromator (not shown in the figure). The incident 103 and transmitted 105 beams (shown, for simplicity, as straight line segments) may be steered using beam deflection control signals generated by the beam deflection control device 112 and delivered via connections, shown as dotted lines, running to the upper 101 and lower 102 beam deflection control circuits of the microscope. The position and/or angle of the incident beam 103 at the plane of the specimen 104 may be changed according to the signal level delivered by the beam control device 112 to the upper beam deflection control circuits 101, typically connected to upper beam dual deflection coils shown as 101A and 101B, and the position and/or angle of the transmitted beam 105 entering the electron energy loss spectrometer 107 may be changed according to the signal level delivered at the lower beam deflection control circuits 102, typically connected to upper beam dual deflection coils shown as 102A and 102B. The beam deflection control device may be aligned and configured to deliver complementary signals to the upper and lower beam deflection control circuits 101 and 102, such that the position of EELS spectrum 108 on EELS detector 109 remains fixed as the incident beam angle and/or position at the sample is changed. The beam control device may be operated manually by the microscope operator, or may be driven by a control computer 113, shown connected to the beam deflection control device 112 via dotted lines. The control computer 113 may also transmit instructions to, and acquire data from, EELS spectrometer 107, EELS detector 109, and EDS detector 110, as shown by the dashed lines in the figure. The beam deflection control device 112 may also be connected to the STEM image detector 106, as also shown by the dashed line in the figure, enabling it to acquire STEM images. (Though not shown in FIG. 1, the STEM image detector 106 may also be connected to control computer 113.) The TEM beam deflection control signals generated by beam control device may typically be delivered at rates between 0.1 Hz and 200 kHz.

Figure 2:
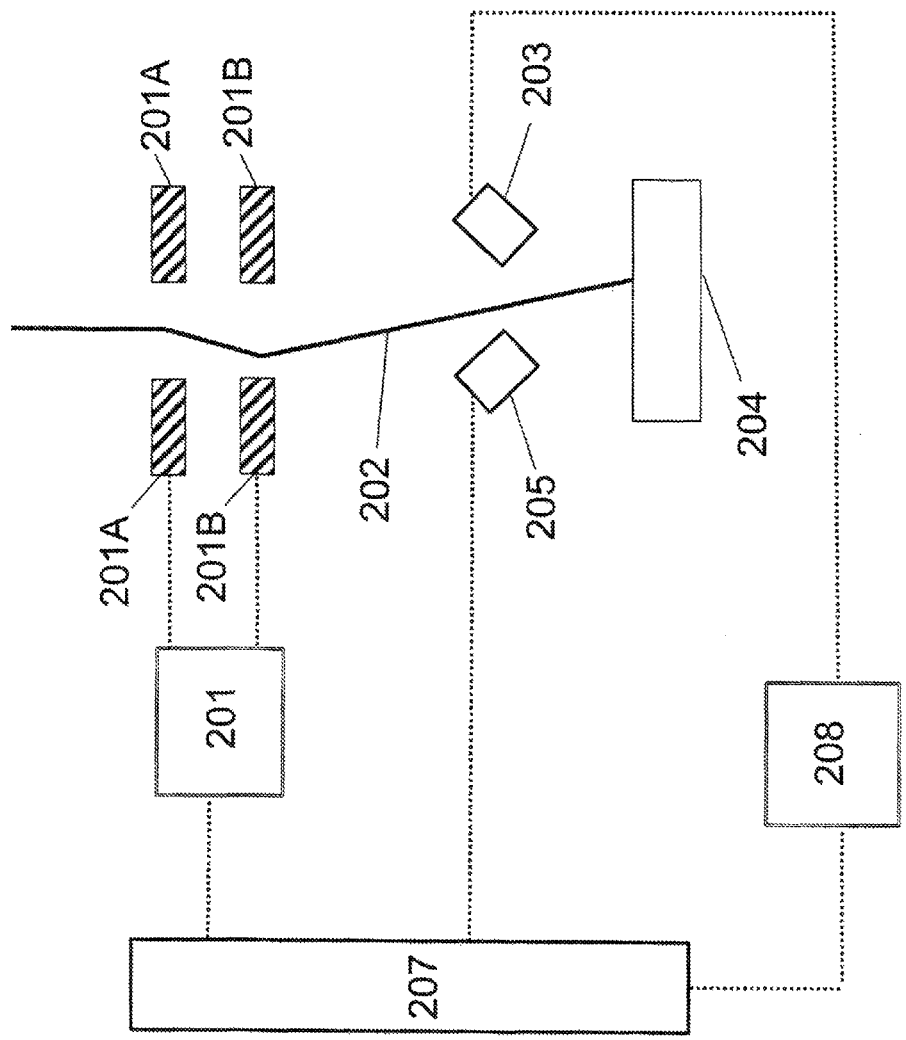
FIG. 2 is a schematic of a SEM configured to practice an embodiment of the invention.

Another embodiment shown in FIG. 2 comprises an SEM, typically with an accelerating voltage in the range between around 10 to 40 kV, coupled to a beam deflection control device 207. Though not shown in FIG. 2, the SEM may be combined with a focused ion beam ("FIB") device. The beam deflection control device 207 may deliver beam deflection control signals to the microscope's beam deflection control circuits 201, via a connection as shown by the dotted lines. The position and/or angle of the incident beam 202 at the plane of the specimen 204 may be changed according to the signal level (typically a voltage signal) delivered to the beam deflection control circuits 201. The beam control device may be operated manually by the microscope operator, or may be driven according to instructions delivered by a control computer 208, shown connected to the beam deflection control device 207 via dotted lines. The control computer 208 may also be connected to the EDS detector 203, as shown by the dotted lines in the figure. The beam deflection control device 207 may also be connected to the SEM image detector 205, in order to acquire SEM images, as illustrated by the dotted lines. (The control computer 208 may also be connected to secondary electron detector 205, though this is not shown in FIG. 2.) The SEM beam deflection control signals may typically be delivered by the beam deflection control device 207 at rates between 0.1 Hz and 200 kHz.

Microscope beam deflection control circuits, shown as 101 and 102 in the TEM configuration shown in FIG. 1, and 201 in the SEM configuration in FIG. 2, generally accept a DC voltage signal, typically in the range of 5 to 20 V. The value of the DC voltage on each input of a beam deflection control circuit (101, 102, or 201) translates into the amount of deflection that circuit will induce in the electron beam. The deflection may typically be produced by pairs of dual-deflection beam coils, each pair comprising upper and lower beam coils, shown as upper coils 101A and 102A and lower coils 101B and 102B in the TEM configuration of FIG. 1, and upper coils 201A and lower coils 201B in the SEM configuration of FIG. 2. (An equal number of orthogonally-disposed dual deflection coils, for inducing deflections outside the plane of the figure, are not shown in FIGS. 1 and 2.) In a dual-deflection coil set, assuming the voltage delivered to the microscope control circuit is faithfully translated into a beam deflection, pure beam tilt with no beam deflection (corresponding to a change incident angle with no change in location at the sample), or pure beam deflection with no beam tilt (corresponding to a change in location with no change in incident angle at the sample) may be induced by maintaining an appropriate fixed ratio between the signal voltage delivered to the upper and lower beam deflection coils.

In one embodiment, the beam deflection control device, shown as 112 in FIG. 1 (and 207 in FIG. 2, contains a series of digital-to analog converters ("DAC"s), one for each beam deflection coil to be addressed in the electron microscope. A typical TEM system having eight such beam deflection coils, counting the orthogonally-disposed coils not shown in FIG. 1, therefore requires eight DACs in the beam deflection control device 112, and a typical SEM system having four beam deflection coils, counting the orthogonally-disposed coils not shown in FIG. 2, therefore requires four DACs in the beam deflection control device 208. Absent distortions, the sequence of voltage values delivered from the DACs to the microscope deflection control circuits may be programmed to deliver a range of different beam scanning protocol signals. For example, in one embodiment, the sequence of voltage values delivered from all eight DACs to a TEM may be synchronized at update rates of 192 kHz, in principle allowing the generation of virtually any form of beam scanning protocol incorporating beam displacement and/or beam tilt above or below the sample.

So as not to degrade spatial resolution, the incident beam scanning protocol should not significantly increase the effective size of the incident beam on the sample by translating the area of the beam substantially beyond the sample location. In EELS, the spectrum formed from the transmitted beam should also remain fixed and having the same entry angle for the detector, so it may be recorded without degrading energy resolution. For elemental (compositional) mapping using EDS or EELS, in which multiple spectra are acquired at different sample locations, but under otherwise nominally identical conditions, synchronization between beam movement and precession may also be required. For example, if the rate at which the beam is moved between locations is not significantly different from the precession rate, synchronization between these rates may be needed to ensure that the beam is incident on each location and spectroscopic data acquired under the same conditions.

Beam scanning protocol signals, for example, delivered by the DACs noted above, may be distorted by the nonlinear response of the microscope beam deflection control circuits. In order to produce the required scanning of the beam, an additional time-dependent nonlinear component (the "distortion compensation signal") may be added to the beam scanning protocol signal.

Further, because the deflection coils in electron microscopes are typically magnetic inductors having a variable frequency response, the deflection signal actually imparted to the electron beam may not match the shape of the beam scanning protocol signal delivered by the microscope deflection control circuits to the deflection coils. In order to compensate for these effects, a time-dependent induction compensation component may be added to the beam scanning protocol signal. One advantage of using circular precession (i.e., keeping the incident angle constant while repeatedly rotating the azimuthal angle through 360°) is that the input signals may be sinusoidal and delivered at a single frequency (the precession frequency), which mitigates the need to account for frequency-dependent induction effects.

As also noted above, in EELS data acquisition, it may be necessary to remove position and angular variations introduced by the incident beam scanning protocol from transmitted/exit beams, in order for the EELS spectrum to remain fixed on the EELS detector and for energy resolution not to be compromised. In principle, a complementary exit beam scanning protocol may be applied using a phase-shifted and appropriately scaled version of the incident beam scanning protocol. For example, for circular precession at a uniform speed of the incident beam, an appropriately scaled and phase-shifted sinusoidal signal may be applied to the lower beam deflection control circuits. In general, additional adjustments to the amplitudes and phases may be required in order to compensate for the time-dependent motion of the exit beam arising from the incident beam scanning protocol, the non-linear behavior of the exit beam deflection circuits and frequency-dependent induction effects in the lower beam deflection coils, as discussed above, and for additional precession of the electron beam caused, in particular, by the magnetic field of the objective lens (referred to here as lens precession). Higher-order objective lens aberrations (generally 3rd-order astigmatism), may also be compensated by addition of a lens aberration signal adjustment.

In view of the above-noted effects, it may be necessary to perform an alignment procedure in order to minimize the above-mentioned distortions of the beam scanning protocol signal by adding small compensations at different phase angles. This procedure may correspond to, for example, adding or subtracting small non-sinusoidal signal amounts from the sinusoidal waveform used to generate a precession scanning protocol. Since each of the above-mentioned distortions, in particular the non-linear behavior of microscope control circuits, may be amplitude- and frequency-dependent, it may be necessary to define a different distortion compensation signals for each combination of precession amplitude and frequency.

In order to avoid inadvertently introducing variability between data sets acquired at different times, or from different locations, a suitably large precession frequency may be selected such that, for each spectrum (or spectroscopic data set) acquired, the beam rotates a large number of cycles (typically more than 100). Alternatively, a smaller, but integral number of precession cycles may be used for the acquisition of each spectrum (or spectroscopic data set). For example, for a spectrum acquired using an integration time of 2 seconds, any frequency greater than about 50 Hz may be acceptable, whereas for an integration time of only 0.1 seconds, any lower frequency that is a multiple of 10 Hz may be applied. (Spectroscopic data set is used here to refer to all or part of a spectrum acquired between a starting and end point, such as those shown in FIGS. 3A and 5, or to all or part of a spectrum acquired between more than one pair of starting and end points.)

Once a precession frequency has been selected, the beam deflection control device may be pre-aligned. This may be done by either selecting a stored set of pre-alignment values, or by adjusting each of the beam deflection control signals to its pre-aligned value. The pre-alignment may be performed at a large precession angle, typically approximately half the maximum feasible precession angle of the microscope system. (The feasible precession angle for a TEM may be significantly less than that available in an SEM.)

An optimum precession angle for a given sample may then be identified by performing a set of quantitative composition measurements, using EELS or EDS, for a range of precession angles on a sample location (or locations) for which the incident beam (before the beam scanning protocol is applied) is oriented along a suitably low-index zone axis. (Examples of such measurements are shown and discussed below for the EELS proof of concept experiments on Si and $SrTiO_3$ shown in FIGS. 3B and 4.) For polycrystalline specimens, which tend to present crystalline grains with a range of different crystallographic orientations relative to the incident beam, the operator may use a small focused beam and observe nano-beam diffraction patterns in order to locate grains which are oriented sufficiently close to a low-index zone axis or axes. For single crystal samples, the user may employ mechanical sample-holder tilts to locate a suitable zone axis condition.

Having identified a location (or locations) of a single- or poly-crystalline sample comprising a suitably oriented crystalline region, the operator may use a beam deflection control device (or instruct a suitably configured external or internal microscope control computer) to acquire a plurality of EDS or EELS spectra over a range of incident precession angles, typically up to some maximum feasible angle determined by the capabilities of the electron microscope. The plurality of spectroscopic data sets may be extracted sequentially, for example, from the lowest to the maximum feasible precession angle. Quantitative data may then be extracted from each spectrum in the plurality and used to determine the precession angle appropriate for a given element. Quantitative composition data may be normalized with respect to data obtained without a beam scanning protocol and displayed, for example, in a Cartesian plot of the type shown in FIGS. 3B and 4. The operator may use such a plot to identify, for example, the minimum precession angle at which signal enhancement saturates, and for which dynamical scattering will not be further suppressed by increasing the precession angle. Identification of such an optimum precession angle may also be performed automatically by the control computer. The precession angle required to saturate a particular compositional signal may vary from element to element between and within different samples (as discussed with reference to the EELS data in FIGS. 3B and 4 below), and as a function of other parameters, such as microscope accelerating voltage.

Having identified an optimum precession angle and frequency, the beam deflection control device may then be aligned at that frequency and amplitude. The alignment may be necessary in order to, for example, account for the nonlinear response of the microscope control circuits, as discussed above. The alignment may be done by either selecting an appropriate set of stored set alignment values, or by appropriately adjusting each of the beam deflection control signals. As noted above, and as indicated by the proof of concept EELS experiments discussed below, the optimum precession conditions—for example, the minimum precession angle required for maximum signal—may vary both from material to material and also within a particular material, depending on the element being investigated.

An incident beam that is sufficiently small in diameter may be scanned between a multiplicity of sample locations and EDS or EELS data acquired at each location. Such location-dependent data—if suitably distributed in a one- or two-dimensional array—may be used to generate a one- or two-dimensional compositional map. The scanning between multiple sample locations may be performed by completing acquisition of a spectroscopic data set at a given location and then moving to other locations, or may be performed by acquiring part of spectroscopic data set at a given location, acquiring data at other locations, and then acquiring more data at the given location. A compositional map may extend over several micrometers in TEM, or even further in SEM, with the total number of data points depending on the spatial extent of the map and the required resolution. A typical one-dimensional composition maps may contain on the order of a few hundred points and typical two-dimensional maps may require hundreds of thousands of points. As the time needed to acquire statistically significant EELS or EDS data may vary from hundredths of a second to tens of seconds per point, total scan times may vary from a few seconds for a one-dimensional map to hours for a two-dimensional map.

Because acquisition of spectroscopic data sets from a multiplicity of sample locations may require a significant amount of time, it may be necessary to compensate for relative shift (drift) between the sample and the incident beam. Drift may originate in, for example, mechanical drift of the specimen stage or electrical drift of the beam deflection circuitry. The direction and magnitude of the drift and the rate of drift may be determined in real time from measurements of SEM/STEM images taken while the data sets are acquired. The anticipated drift at a particular future sample location may be extrapolated from the last measured drift and drift rate, and a deflection signal, equal in amplitude but opposite in direction to the extrapolated drift, added in real time to the beam deflection values at each sample location. The success of the drift adjustment may also be verified after the fact by measuring successive SEM/STEM images obtained from different sample locations. For drift compensation, an image of approximately 100 by 100 pixels, providing sufficient resolution to make comparisons and ascertain drift, may be acquired in typically around one second.

In TEM, data may be acquired using a large (significantly greater than 10 nm diameter) semi-parallel beam or a small (typically under 10 nm in diameter), convergent beam focused on the sample. When acquiring EELS or EDS data from a few sample locations, either mode may be appropriate, assuming a suitable geometry sample is available. However, when acquiring data from a multiplicity of closely-spaced sample locations, as may be required for a compositional map, the small convergent beam is used in certain embodiments. In SEM, on the other hand, the beam is typically focused and convergent.

Example 1

EELS

Proof of concept EELS experiments were conducted using a JEOL 2010 F TEM coupled to a Gatan Imaging Filter and a NanoMEGAS SpinningStar precession system (designed for and marketed for structural analysis of crystalline materials using PED). A 0.5 nm probe with a 9 mrad (approx. 0.5°) convergence and 10 mrad (approx. 0.6°) collection semi-angle was used in conjunction with precession angles between 0 and 1.92°. The precession frequency was set at 100 Hz and the microscope operating voltage at 200 keV.

Figure 3A:
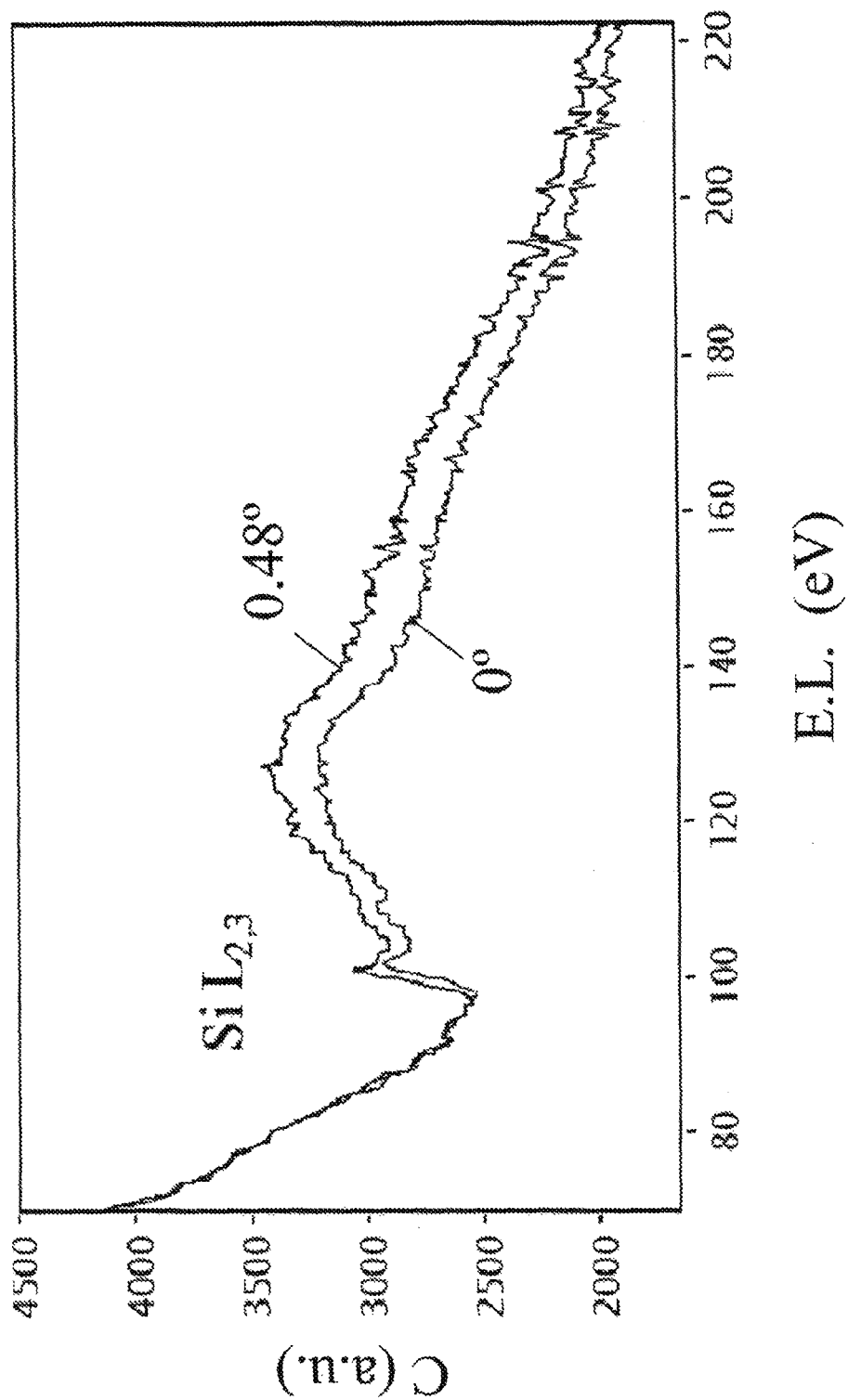
FIG. 3A shows a Si $L_{2,3}$ peak without and with precession at a 0.48° angle.
Figure 3B:
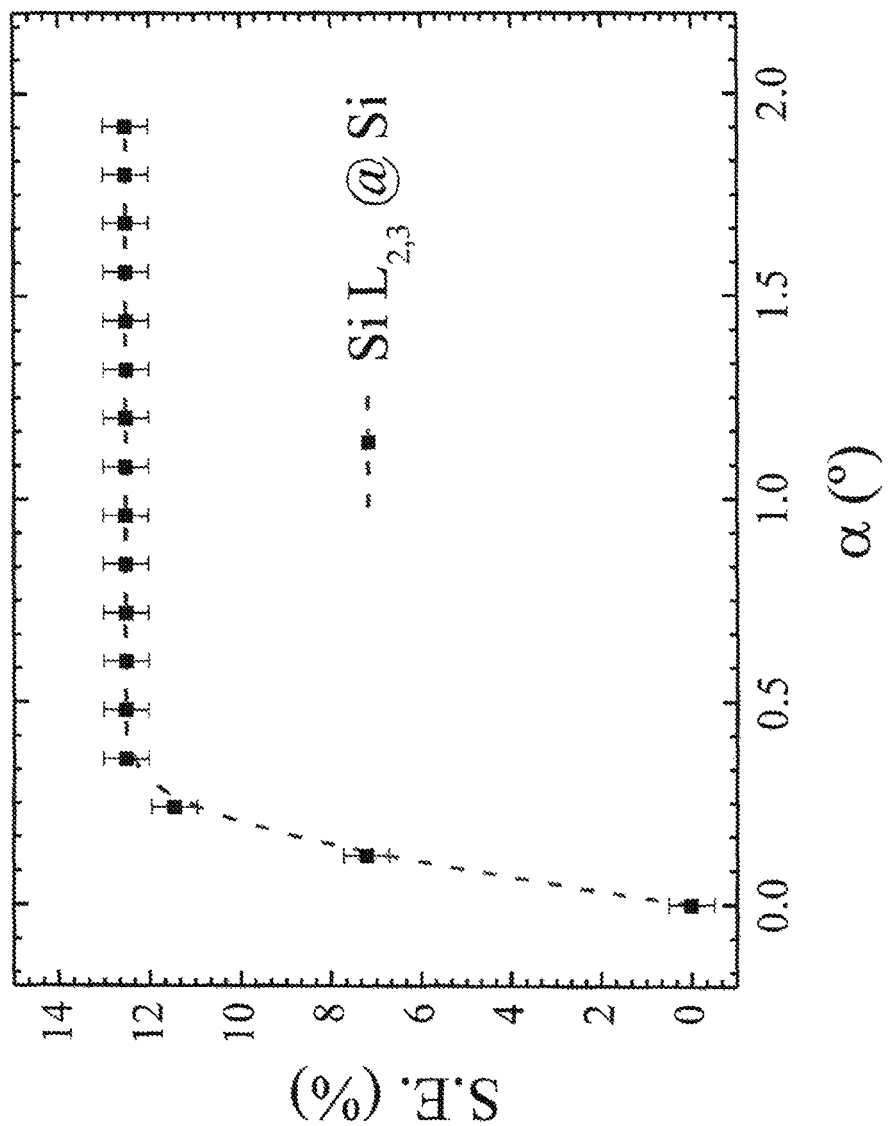
FIG. 3B shows a Si $L_{2,3}$ peak signal enhancement as a function of precession angle

A first proof of concept experiment was conducted using the Si $L_{2,3}$ peak (edge) obtained from a single crystal Si sample oriented along the [011] zone axis. Spectra containing the Si $L_{2,3}$ peak were acquired over 3 s periods at range of precession angles. FIG. 3A shows raw data, counts (C) expressed in arbitrary units (a.u.) plotted against energy loss (E.L.) expressed in eV, for the Si $L_{2,3}$ spectral region acquired without precession and at a 0.48° precession angle. The qualitative enhancement of the Si $L_{2,3}$ signal with a 0.48° precession angle is apparent. A quantitative assessment of the enhancement was performed by extracting the background from each spectrum and integrating the signal over a 100 eV energy range to obtain the peak intensity (I). The signal enhancement (SE) for a given precession angle ($\alpha$) can then be expressed as the ratio $(I(\alpha)-I(0))/I(0)$, where $I(0)$ is the intensity without precession. FIG. 3B is a plot of SE, expressed as a percentage, against precession angle ($\alpha$) between 0 (no precession) and 1.92° and shows Si $L_{2,3}$ signal enhancement increasing with precession angle and then saturating at an angle of only around 0.5°. Surprisingly, the saturation in the EELS signal occurs at a much lower angle than the 2 to 3 degrees typically required to suppress dynamical effects in quantitative transmission electron diffraction.

Figure 4:
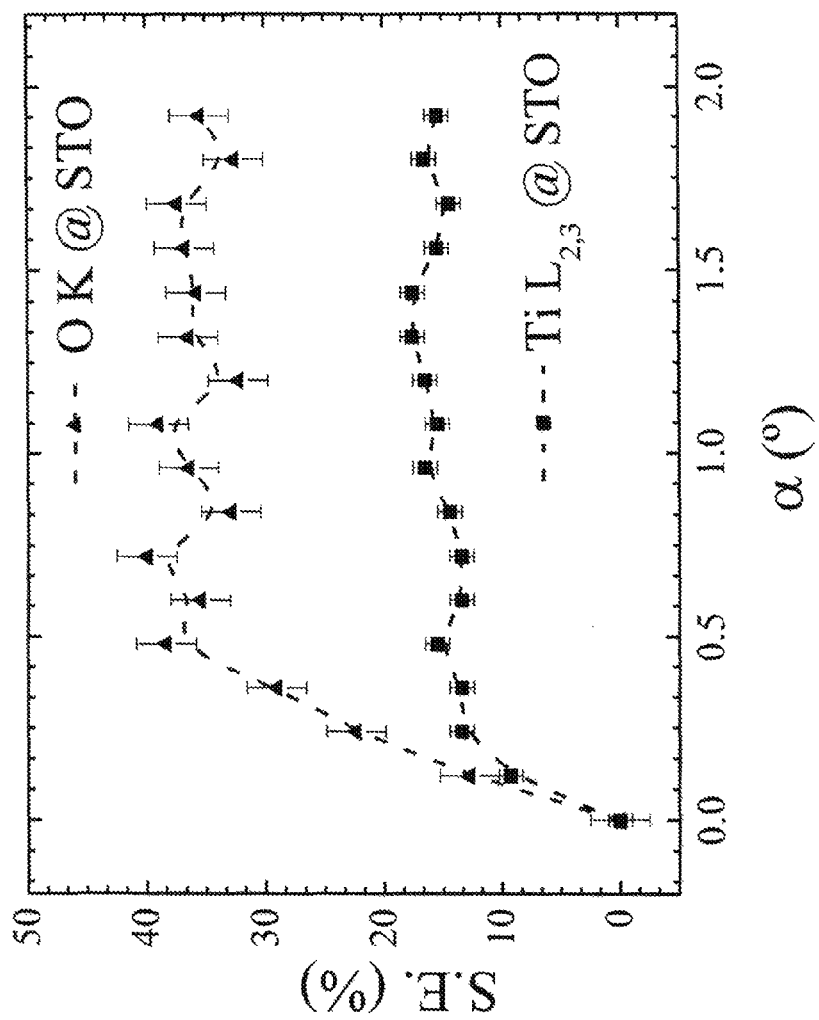
FIG. 4 shows Ti $L_{2,3}$ and O K signal enhancement as a function of precession angle

A second proof of concept experiment was conducted using the O K and Ti $L_{2,3}$ peaks acquired from a single crystal $SrTiO_3$ ("STO") sample oriented along the [001] zone axis. Spectra containing the O K and Ti $L_{2,3}$ peaks were acquired over 6 s periods at range of precession angles. As for the Si data above, a quantitative assessment of signal enhancement for the STO data was undertaken by extracting the background from each spectrum and integrating the peak signals over, in this case, a 50 eV energy range to obtain O K and Ti $L_{2,3}$ peak intensities. Calculated as for the Si data above, FIG. 4 is a plot of SE, expressed as a percentage, for precession angles ($\alpha$) between 0 (no precession) and 1.92° and shows an increase in the SE for the O K and Ti $L_{2,3}$ edges with increasing with precession angle. Though the STO data is noisier than the SI data shown in FIG. 3B, the same saturation with increasing angle is observed, but at a saturation angle apparently lower than the around 0.5° seen in the Si data.

Example 2

EDS

Proof of concept EDS experiments were conducted using a JEOL 2100 $LaB_6$ TEM coupled to: a) an Oxford Inca EDS detector model 6498 with a take-off angle of 22 degrees, a detector area of 30 mm² and an energy resolution of 136 eV at 5.9 KeV; and b) a NanoMEGAS DigiStar precession system model P1000. A 25 nm probe with a 2 mrad (0.12 degrees) convergence angle was used in conjunction with precession angles between 0 and 3 degrees. The precession frequency was set at 100 Hz and the microscope operating voltage was 200 keV.

A sample of single crystal silicon was aligned precisely along the [110] zone axis and the SiK$\alpha$ peak measured with precession inclination angles of 0, 1, 2 and 3 degrees. A maximum increase in signal strength of approximately 8% in the strength of the Si peak was observed.

Figure 5:
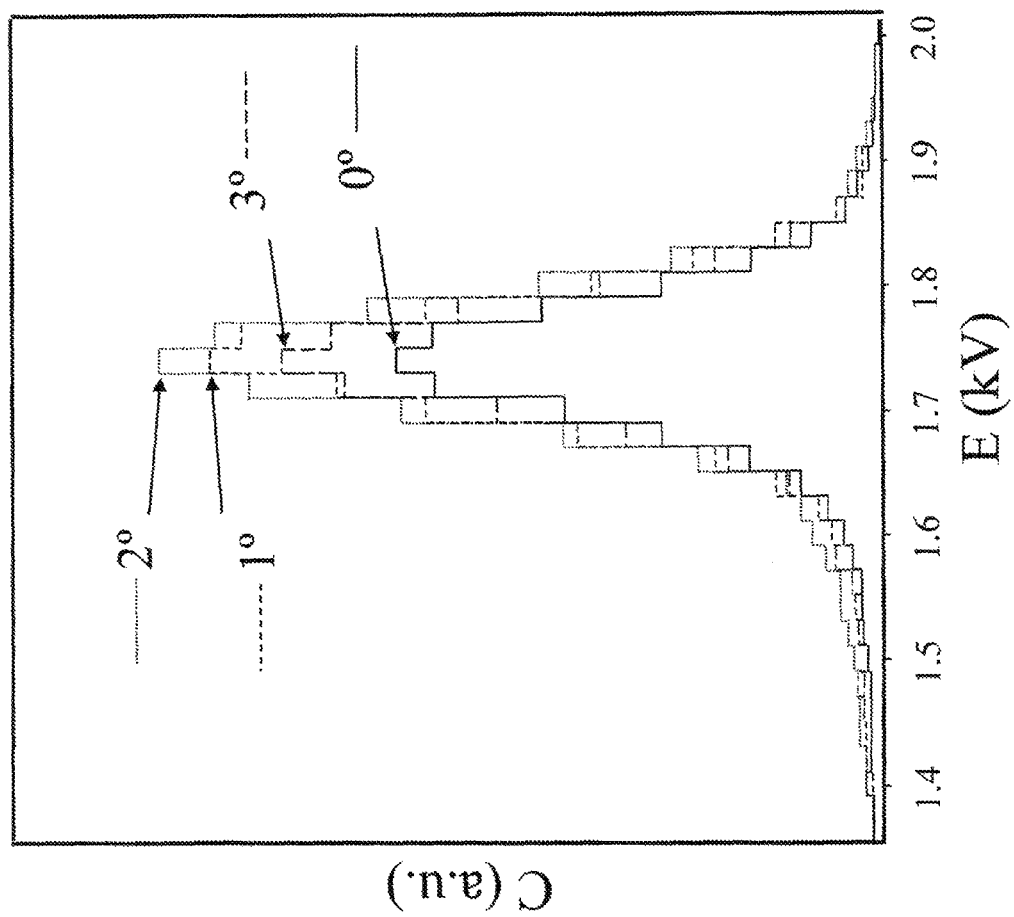
FIG. 5 shows Si K-alpha signal without precession and with precession at angles of 1, 2 and 3°.

FIG. 5 displays an overlay of the different SiK$\alpha$ peak signals acquired at different precession angles after background normalization. Data labeled 0 was acquired without precession, and that labeled 1, 2 and 3 with precession angles of 1, 2 and 3 degrees, respectively. Counts (C) in arbitrary units (a.u.), with the full scale corresponding to 506 counts, are plotted against x-ray energy given in kV. The increase in SiK$\alpha$ signal strength with increasing precession angle is evident for 1 and 2 degree precession angles. However, unlike the Si and STO EELS data in FIGS. 3 and 4, the measured EDS signal does not appear to saturate with increasing precession angle, rather the SiK$\alpha$ signal strength decreases as the precession inclination angle is increased from 2 to 3 degrees.

Numerical ranges cited herein are intended to recite not only the end values of such ranges but the individual values encompassed within the range and varying in single units of the last significant figure. By way of example, a range of from 0.1 to 1.0 in arbitrary units according to the present invention also encompasses 0.2, 0.3, 0.4, 0.5, 0.6, 0.7, 0.8, and 0.9; each independently as lower and upper bounding values for the range.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

Patent documents and publications mentioned in the specification are indicative of the levels of those skilled in the art to which the invention pertains. These documents and publications are incorporated herein by reference to the same extent as if each individual document or publication is specifically and individually incorporated herein by reference.

The invention claimed is:

1. A method for improving characteristic peak signal strength in electron energy loss data comprising:
    furnishing in a transmission electron microscope a sample comprising crystalline material;
    configuring an electron beam to impinge on a location of the sample comprising a region of crystalline material;
    applying, by tilting the electron beam, an incident beam scanning protocol that maintains the incident beam impinging substantially on the sample location while varying over time one or both of the incident beam inclination angle and azimuthal angle, the incident beam scanning protocol being configured to impart a net inclination to the incident beam to suppress dynamical scattering;
    acquiring, from an electron beam exiting the sample, electron energy loss data comprising at least part of a characteristic energy loss peak while the incident beam scanning protocol is being applied;

determining an optimum net inclination at which signal enhancement of said characteristic electron energy loss peak is substantially saturated; and, acquiring electron energy loss data at said optimum net inclination.

2. The method of claim 1, further comprising applying a complementary beam scanning protocol to the exit beam that substantially removes any time-dependent motion of the exit beam arising from the incident beam scanning protocol.

3. The method of claim 1, further comprising the step of extracting quantitative compositional information from the electron energy loss data acquired at said optimum net inclination.

4. The method of claim 1, wherein the incident beam scanning protocol comprises processing the incident beam at a substantially constant inclination angle.

5. The method of claim 1, wherein the incident electron beam without the beam scanning protocol applied is substantially parallel with a high symmetry crystallographic direction of the crystalline region.

6. The method of claim 1, wherein the optimum net inclination is the minimum net inclination for which the signal enhancement of the characteristic peak obtains its maximum value.

7. A The method of claim 3, further comprising:
acquiring electron energy loss data while applying said incident beam scanning protocol at said optimum net inclination at a multiplicity of sample locations;
extracting quantitative compositional information from the electron energy loss data acquired at each of said multiplicity of sample locations, and
mapping the quantitative compositional information obtained from the multiplicity of sample locations and the relative location of the multiplicity of sample locations onto a compositional map.

8. The method of claim 1, wherein the transmission electron microscope comprises a number of beam deflection control circuits and the beam scanning protocol is applied by delivering a scanning protocol signal to at least a fraction of the number of beam deflection control circuits.

9. The method of claim 8, wherein at least one of the beam scanning protocol signals further comprises one or more of an induction compensation component, a distortion compensation component, a lens precession component, and a lens aberration component.

10. A method for improving characteristic peak signal strength in energy-resolved x-ray data comprising:
furnishing in a transmission electron microscope a sample comprising crystalline material;
configuring an electron beam to impinge on a location of the sample comprising a region of crystalline material;
applying, by tilting the electron beam, an incident beam scanning protocol that maintains the incident beam impinging substantially on the sample location while varying over time one or both of the incident beam inclination angle and azimuthal angle, the incident beam scanning protocol being configured to impart a net inclination to the incident beam to suppress dynamical scattering;
acquiring from x-rays emitted from the crystalline region energy-resolved x-ray data comprising at least part of a characteristic x-ray peak while the incident beam scanning protocol is being applied;
determining an optimum net inclination at which signal enhancement of said characteristic x-ray peak is substantially saturated; and acquiring energy-resolved x-ray data at said optimum net inclination.

11. The method of claim 10, further comprising applying a complementary beam scanning protocol to the exit beam that substantially removes any time-dependent motion of the exit beam arising from the incident beam scanning protocol.

12. The method of claim 10, further comprising the step of extracting quantitative compositional information from the energy-resolved x-ray data acquired at said optimum net inclination.

13. The method of claim 10, wherein the incident beam scanning protocol comprises processing the incident beam at a substantially constant inclination angle.

14. The method of claim 10, wherein the incident electron beam without the beam scanning protocol applied is substantially parallel with a high symmetry crystallographic direction of the crystalline region.

15. The method of claim 10, wherein the optimum net inclination is the minimum net inclination for which the signal enhancement of the characteristic peak obtains its maximum value.

16. The method of claim 12, further comprising:
acquiring energy-resolved x-ray data while applying said incident beam scanning protocol at said optimum net inclination at a multiplicity of sample locations;
extracting quantitative compositional information from the energy-resolved x-ray data acquired at each of said multiplicity sample locations, and
mapping the quantitative compositional information obtained from the multiplicity of sample locations and the relative location of the multiplicity of sample locations onto a compositional map.

17. The method of claim 10, wherein the transmission electron microscope comprises a number of beam deflection control circuits and the beam scanning protocol is applied by delivering a scanning protocol signal to at least a fraction of the number of beam deflection control circuits.

18. The method of claim 17, wherein at least one of the beam scanning protocol signals further comprises one or more of an induction compensation component, a distortion compensation component, a lens precession component, and a lens aberration component.

19. A system for improving characteristic peak signals in electron energy loss or energy-resolved x-ray data obtained in a transmission electron microscope,
the system comprising an external beam control device comprising a number of DACs, each DAC being configured to deliver a beam scanning protocol signal to one of a number of beam deflection control circuits of the transmission electron microscope,
the system being configured to:
implement, by delivering a suitably configured combination of beam scanning protocol signals to at least a fraction of the number of beam deflection control circuits of the transmission electron microscope, an incident beam scanning protocol that maintains the incident beam impinging substantially on a sample location while varying over time one or both of the incident beam inclination angle and azimuthal angle, thereby imparting sufficient net inclination to the incident beam to suppress dynamical scattering;
acquire electron energy loss data comprising a characteristic peak and/or energy-resolved x-ray data comprising a characteristic peak while the incident beam scanning protocol is being applied;

determine an optimum net inclination at which signal enhancement of the characteristic peak is substantially saturated; and acquire the electron energy loss data and/or energy-resolved x-ray data at said optimum net inclination.

20. The system of claim 19, being further configured to implement, by delivering a suitably configured combination of beam scanning protocol signals to at least a further fraction of the number of beam deflection control circuits of the transmission electron microscope, a complementary exit beam scanning protocol that substantially removes any time-dependent motion of the exit beam arising from the incident beam scanning protocol.

21. The system of claim 19, wherein at least one of the beam scanning protocol signals further comprises one or more of an induction compensation component, a distortion compensation component, a lens precession component, and a lens aberration component.

22. The system of claim 19, further comprising a control computer configured to drive the external beam control device and to acquire and process electron energy loss and/or energy-resolved x-ray data.

23. The system of claim 19, wherein the external beam control device is further configured to compare images received at different times from a microscope detector and apply drift compensation.

* * * * *